United States Patent [19]

Haner

[11] Patent Number: 5,002,063

[45] Date of Patent: Mar. 26, 1991

[54] ELECTRONIC PHYSIOLOGICAL DATA MONITORING

[75] Inventor: Lambert Haner, Rocky River, Ohio

[73] Assignee: The Scott Fetzer Company, Westlake, Ohio

[21] Appl. No.: 501,557

[22] Filed: Mar. 29, 1990

[51] Int. Cl.[5] ............................................. A61B 5/04
[52] U.S. Cl. ...................................... 128/696; 128/706
[58] Field of Search ............... 128/696, 702, 706, 710; 364/413.05, 413.06

[56] References Cited

U.S. PATENT DOCUMENTS

| | | | |
|---|---|---|---|
| 3,602,706 | 8/1971 | Levitt | 128/696 |
| 4,261,369 | 4/1981 | Allov | 128/696 |
| 4,417,306 | 11/1983 | Citron et al. | 364/413.06 |
| 4,679,568 | 7/1987 | Blau et al. | 128/696 |
| 4,865,039 | 9/1989 | Dunseath, Jr. | 128/696 |
| 4,913,146 | 4/1990 | DeCote, Jr. | 128/696 |

OTHER PUBLICATIONS

Medical Instrumentation, Application and Design, John G. Webster, editor, Houghton Mifflin Co., Boston, pp. 308–309.

*Primary Examiner*—Francis Jaworski
*Assistant Examiner*—George Manuel
*Attorney, Agent, or Firm*—Watts, Hoffman, Fisher & Heinke Co.

[57] ABSTRACT

An ECG system is disclosed having amplification circuitry which, while effectively blocking electrical transients resulting from undesirable low frequency electrical artifacts, nevertheless maximizes the continuity of receipt of desirable heart activity indicating information. The ECG system employs a DC coupled amplifier including an integrating circuit for effectively reducing the DC gain of the amplifier to substantially zero and for providing a pass band gain of about 1,000 at frequencies above about 0.05 Hz. A fast acting saturation sensing circuit is also incorporated. The saturation sensing circuit resets the integrating circuit to offset any artifact produced signal and to thereby minimize loss of the desired ECG hear activity indicating information.

18 Claims, 2 Drawing Sheets

ELECTRONIC PHYSIOLOGICAL DATA MONITORING

TECHNICAL FIELD

This invention relates generally to the field of electronic physiological data monitoring, and more particularly to electrocardiographic monitoring employing improved amplification characteristics.

BACKGROUND ART

It is well known to evaluate the condition of a patient's heart by monitoring electrical signals produced by the heart and storing and/or displaying a representation of these continuously monitored heart activity indicating signals on a suitable medium, such as by means of a strip chart recorder or a cathode ray tube. The recording or display takes the form of a waveform describing heart electrical output versus time which is known as an electrocardiogram, sometimes abbreviated ECG.

The electrical signals representing heart activity are conventionally picked up by a combination of three electrodes. Each electrode is applied to a portion of the patient's body through an interface of a conductive gel to improve conductivity and to lessen electrical artifacts which occur in the course of an ECG study. Each electrode is connected by an electrical cable to an electronic unit which is sometimes called a portable acquisition unit.

The purpose of the portable acquisition unit and its amplifier circuitry is to condition the electrical heart activity indicating signals of physiological origin so that they can be transmitted from the body to the heart activity display and recording apparatus.

There are two basic problems associated with the extraction of the heart activity indicating information. First, the signal amplitude is very low coming from a fairly high source impedance. Secondly, the heart activity indicating signals exist in the presence of significant extraneous "noise" signals. The noise signals originate from low frequency and high amplitude artifacts. These artifacts are created by the electrode interface used to sense the physiological signals and also from slightly higher frequency (60, 120 Hz.) electromagnetic interference, as well as from physical phenomena relating to the electronic circuit elements.

In a conventional ECG system, a first electrode is attached to the patient's side, a second electrode is attached near the patient's sternum, and a third, or reference, electrode is attached to the patient's right leg or abdomen. The first and second electrodes produce the heart activity signals.

Despite the use of the conductive gel, the electrical artifacts still occur superimposed on the desirable heart activity indicating signals. These artifacts often have an amplitude much greater than that of the heart activity indicating signals, and consequently, when they occur, they swamp out the useful information contained in the heart activity indicating signals whose monitoring is desired. More specifically, the heart activity indicating signals are usually in the one millivolt range, while the artifacts are in the 20-30 millivolt range, and can run as high as about 200 millivolts.

Typically, the circuitry of the portable acquisition unit has a dynamic range which enables the unit to accommodate incoming heart activity indicating signals up to about 5 millivolts. Any signals greater than that value, including artifact signals, will drive the electronic circuitry of the portable acquisition unit into saturation, and will thus obliterate any desirable information component of heart-generated electrical signals being received at the time of occurrence of the artifact. The problem of these artifacts is exacerbated by the fact that the portable acquisition unit typically includes a high gain amplifier for amplifying the heart activity indicating signals to render them suitable for driving the strip chart recorder or for actuating a cathode ray tube (CRT) display which provides a real time display of the waveform of the heart activity indicating signals.

Common forms of portable acquisition units have included a differential preamplifier. The differential preamplifier receives electrical signals from the cables connected to the first and second electrodes described above. The differential preamplifier produces a continuous real time output signal which is a function of the difference between the signals on the first and second electrodes. The preamplifier stage also amplifies this difference signal by a small gain.

The output of the differential preamplifier stage is directed to other downstream circuitry of the portable acquisition unit. The downstream circuitry provides additional or main amplification, to raise the total gain to something in the neighborhood of 1,000. The downstream circuitry can also provide for other forms of desirable signal processing to render the signal more appropriate for driving the real time display or the strip chart recorder or any other form of signal storage device.

Circuitry has been provided to reduce the undesirable effects of electrical artifacts superimposed on the desirable heart activity indicating signals. One such technique has been to "AC couple" the differential preamplifier stage to the downstream circuitry. This has been done by interposing an AC coupling capacitor in series in the path of the output signal from the preamplifier. In such an embodiment, a resistor is added between the downstream terminal of the capacitor and ground.

The capacitor blocks transmission of DC or very low frequency signals before they reach the downstream circuitry containing the main amplifier. Since the artifacts often take the form of a sharp change in overall DC level, or are of very low frequency, the capacitor is effective in blocking out the electrical artifacts which make their way through the preamplifier stage.

A significant problem with this approach is that, during the time that the blocking capacitor and its associated resistor are responding to transients caused by the electrical artifacts in order to block those transients, they are also blocking the transmission of the useful hard activity indicating signals. In order to block the undesirable transients, the capacitor responds by storing up electrical charge resulting therefrom, and by subsequently and relatively slowly discharging that extra charge through the associated resistor to ground. In order to be effective, the capacitance of the capacitor and the value of the associated resistor must be chosen such that the time constant of this RC combination is on the order of 3 seconds. This means that, when a transient occurs and is blocked and drained off by the RC combination, the useful information borne by the heart activity indicating signals is also effectively blocked from the downstream circuitry for a period at least equal to the time constant of the RC combination, and often, in practice, for a much longer time than that, i.e., on the order of 10 or 11 seconds.

Thus, when AC coupling is employed to block transients resulting from undesirable electrical artifacts, there occurs a time window associated with each artifact during which the desirable heart activity indicating information is not transmitted either. This creates a very undesirable discontinuity in the receipt and recording of heart activity indicating information.

It is a general object of this invention to provide an ECG system having circuitry which, while effectively blocking electrical transients resulting from artifacts, nevertheless maximizes the continuity of receipt of desirable hear activity indicating information.

DISCLOSURE OF THE INVENTION

This invention constitutes an ECG system which employs an amplifier which is designed to substantially eliminate the problem of loosing the ECG heart activity signals during the recovery time constant of the prior art AC coupled circuit.

The ECG amplifier embodied in the present invention is DC coupled from its input all the way to its output, rather than being AC coupled, as in the prior art. The amplifier includes an integrating circuit to effectively reduce the DC gain of the amplifier to zero and to provide a pass band gain of about 1,000 at frequencies above about 0.05 Hz. A fast acting saturation sensing circuit is also incorporated. The saturation sensing circuit resets the integrating circuit to offset any artifact produced signal and to thereby prevent loss of the desired ECG heart activity indicating signal.

These and other advantages of the present invention will be understood in more detail by reference to the following detailed description, and to the drawings, in which:

BEST MODE FOR CARRYING OUT THE INVENTION

Figure 1A:
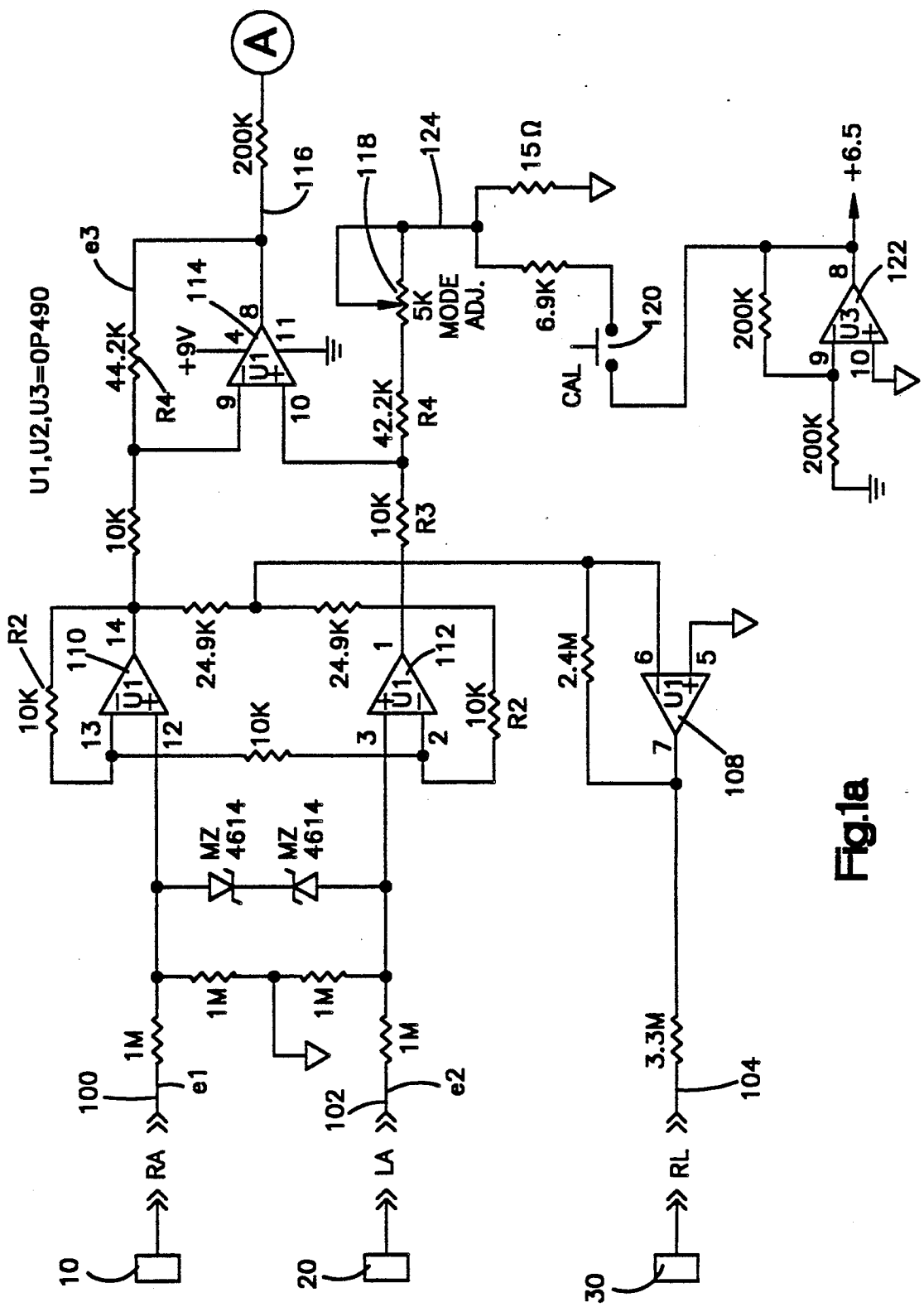
FIGS. 1a and 1b are schematic electrical circuit drawings illustrating the preferred embodiment of the amplification circuitry of an ECG system of the present invention.
Figure 1B:
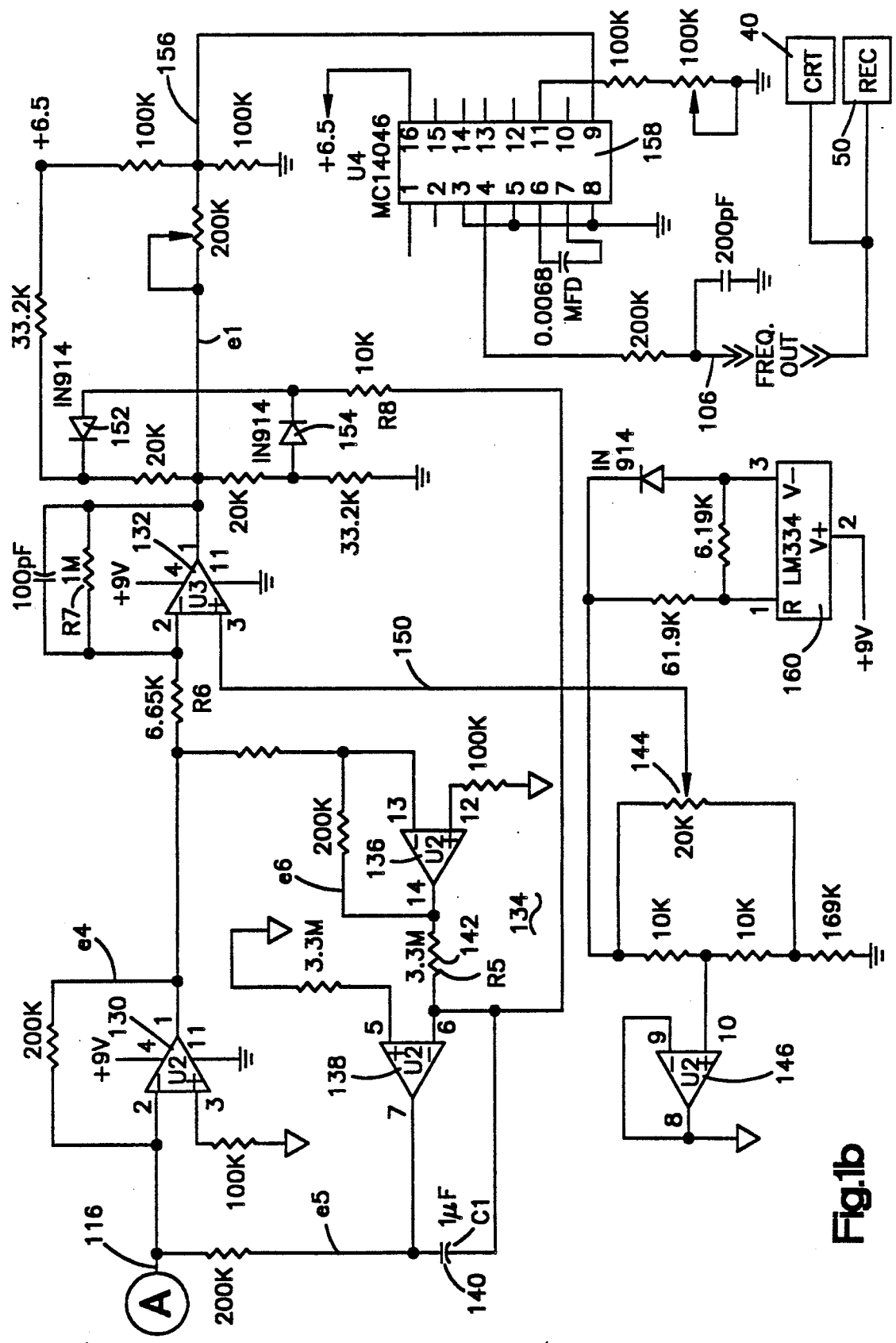

FIGS. 1a and 1b, taken in conjunction, illustrate an ECG system having the circuitry embodied in the present invention for producing heart activity indicating ECG signals. The circuitry of FIGS. 1a and 1b has three inputs and one output. Inputs appearing at the leads 100, 102, 104 carry heart activity indicating signals derived from electrodes 10, 20, 30 and associated cables attached to the patient's body. Referring to FIG. 1b, an output appears at a lead 106 which is an AC signal having a frequency which is a function of the instantaneous amplitude of the heart activity signals appearing at the input leads 100, 102, 104.

The input lead 100 is conductively connected by a cable to an electrode 10 shown) attached in the area of the patient's sternum. The lead 102 is connected by means of a cable to an electrode 20 attached in the patient's rib cage area. The lead 104 is attached by means of a cable and electrode 30 to the patient's right leg, abdomen or other suitable location for providing a body reference voltage signal.

In practice, where extremely precise ECG data is not required, but rather only a generally approximate heart activity waveform is required, the lead 104 and operational amplifier 108 can be omitted from the circuitry.

Signals from the inputs 100, 102 are directed as inputs to operational amplifiers 110 and 112, respectively. Outputs from the operational amplifiers 110, 112 are directed as inputs to an operational amplifier 114. Together, the operational amplifiers 110, 112, 114, and their associated circuitry, form a differential preamplifier. The output of the differential preamplifier, appearing at a lead 116, is a function of the instantaneous difference between the values of the signals appearing at the inputs 100, 102.

In such a differential amplifier, it is desirable to reduce as much as possible the common mode of the output signal appearing at the lead 116. In order to accomplish this, a potentiometer 118 is provided. In practice, the potentiometer 118 is adjusted to minimize the common mode signal appearing at the lead 116. When this is done, one has minimized the common mode component of the output signal appearing at the lead 116.

The gain of the differential preamplifier is approximately 6.5.

Circuitry is provided for, in the absence of input signals at the leads 100, 102, introducing a constant test, or calibration, signal to the differential preamplifier output. This is accomplished by a switch 120 in conjunction with an operational amplifier 122. When the calibration switch 120 is depressed and held, a voltage is produced on a lead 124 which eventually find its way to the plus input of the operational amplifier 114. This voltage is chosen and adjusted to simulate the results which would ensue from a 1 millivolt potential difference appearing between the leads 100, 102. While the switch 120 is depressed, the remainder of the circuitry can be adjusted and calibrated as need be.

The circuitry of FIGS. 1a and 1b are joined via the single lead 116, which has a common terminal identified generally in both drawings by the large character "A". The signal from the lead 116 proceeds through an operational amplifier 130, whose output is transmitted as an input to another operational amplifier 132. The operational amplifiers 130 and 132 constitutes a main amplifier stage of the circuitry of FIGS. 1a and 1b. The operational amplifier 130 has adjustable gain and is associated with adjusting the overall gain of the main amplifier stage as a function of frequency, by way of an integrating circuit which will now be described in more detail.

The integrating circuit, generally designated as 134, includes operational amplifiers 136, 138, and their associated circuitry. The integrating circuit 134 operates to adjust the effective gain of the amplifier 130 between approximately unity and zero. The integrating circuit 134 causes the gain of the amplifier 130 to be substantially 0 at DC, and to rise with frequency to unity.

The gain versus frequency function of the amplifier 130, in conjunction with the integrating circuit 134, defines a roll-off region in the gain versus frequency curve of the amplifier 130. The location of this roll-off is a function of the time constant determined by the value of a capacitor 140 (also designated $C_1$) and of a resistor 142 (3.3 megohm). In the preferred embodiment, the values of the capacitor 140 and the resistor 142 are chosen such that the roll-off is located at approximately 0.05 Hz.

Circuitry, including a potentiometer 144 and an operational amplifier 146, is provided for adjusting the offset of the amplifier 132. Preferably, the potentiometer 144 is adjusted to provide approximately 3.25 volts offset, applied over a lead 150 to the main amplifier 132.

Diodes 152 and 154 comprise a saturation sensing circuit. When the output from the amplifier 132 is above 2.5 volts, or below minus 2.5 volts, with respect to the reference level voltage, one of the diodes will conduct and cause the integrating circuit 134 to quickly reset its offset. Resetting the offset facilitates recentering the dynamic range of amplifier 132 with respect to the DC current level then obtaining.

The output from the main amplifier 132 is transmitted along a lead 156 as an input to an integrated circuit 158. The integrated circuit 158 is configured as a voltage controlled oscillator (VCO). The VCO 158 produces at the output 106 an AC signal whose frequency varies as a function of the magnitude of the instantaneous voltage appearing on the lead 156. Since the lead 156 carries a fluctuating voltage which represents the waveform of heart activity being monitored by the ECG system, the frequency of the output 106 varies in accordance with the profile of that waveform.

The varying frequency signal appearing at the lead 106 can be used in a variety of ways to drive peripheral equipment for displaying and/or recording the representation of heart activity. For example, the signal appearing at the lead 106 can be used to frequency modulate a carrier signal, which can be transmitted by a miniature radio transmitter near the patient's body to a receiver. At the receiver, the FM signal is decoded and the resulting decoded signals can be used in known ways to provide recorded information (on a recorder 60) describing heart activity, and/or a real time display, such as on a cathode ray tube (CRT) 50. Alternately, the signal at the output 106 can be used to drive a light emitting diode (LED). The varying light output on the LED can be transmitted to a remote location by the use of a fiber optic cable, where the information can be decoded, recorded, and/or displayed in real time.

A precise level of current for the circuit of FIGS. 1a and 1b is provided by a current source 160.

The circuit is powered by a 9 volt dry cell battery. The circuit is designed to minimize the current drain from the battery so that we obtain a reasonably long period of operation from a given battery. Also, the circuit requires a stable reference voltage which cannot be the battery voltage because that will vary as it drains. Circuit 160 is a precision current source which feeds the resistors 10k, 10k and 169k connected to 146 to develop the precision reference voltage. This only drains 20 microamps from the battery. A regulator integrated circuit, on the other hand, would draw as much as 3 to 6 milliamps from the battery.

The circuitry of FIGS. 1a and 1b will now be described in greater mathematical detail and in terms of the results accomplished by this circuitry.

The purpose of the circuitry of FIGS. 1a and 1b is to condition electrical signals representing physiological phenomena so that they can be transmitted from the body, displayed, and/or stored. Among the purposes of the present embodiment is the facilitation of cardiac rehabilitation.

The ECG electrical signals from the patient's body appearing at the input terminals 100, 102 are also designated, in FIG. 1a, as $e_1$ and $e_2$.

As mentioned above, the differential preamplifier produces a signal which is a function of the difference $e_2-e_1$, and ideally rejects the common mode signals. The common mode rejection ratio is about 85 db. The preamplifier gain expressing $e_3$ relative to $e_2-e_1$ is:

$$\frac{e_3}{e_2 - e_1} = \frac{1}{2}\left[1 + \frac{2R_2}{R_1}\right]\left[\frac{R_4}{R_3}\right] \quad \text{Eq. (1)}$$

When one inserts the designated circuit values in equation (1), one obtains:

$$\frac{e_3}{e_2 - e_1} = \frac{1}{2}\left[1 + \frac{2 \times 10 \text{ k}}{10 \text{ k}}\right]\left[\frac{44.2 \text{ k}}{10 \text{ k}}\right] = \frac{1}{2}[1 + 2][4.42] = 6.63 \quad \text{Eq. (2)}$$

The differential preamplifier is DC (direct coupled), and has a flat gain versus frequency curve over the entire range of interest, i.e., up to about 100 Hz. The upper frequency limit is determined by the characteristics of the operational amplifiers constituting the differential preamplifier.

The nominal ECG gain $$\frac{e_{out}}{e_2 - e_1}$$

is preferably about 1,000, where $e_{out}$ is the signal designated as $e_7$ in FIG. 1b. This gain will produce about a 1 volt ECG signal at $e_7$ for a 1 millivolt signal difference $e_2$-$e_1$. The linear dynamic range of $e_7$ is 5 volts total. Therefore, a 5 millivolt signal at $e_2$-$e_1$ will saturate the output at $e_7$. This is a problem for a conventional DC amplifier with a gain of 1,000 because the artifact signal (slowly varying DC potentials from the source) can be 200 or 300 millivolts in amplitude, though they are more commonly 10 to 30 millivolts. The ECG signal of interest does not have information at the DC range, but the ECG signal is a low frequency (1 pulse per second) signal and in order to pass its waveform information without distortion, it is necessary to have the low frequency pass band extend down to about 0.05 Hz. The circuitry of FIGS. 1a and 1b is DC coupled from input to output, but uses the integrating circuit 134 to effectively reduce the DC gain to zero and to allow a pass band gain of about 1,000 at frequencies of about 0.05 Hz. Also the fast acting saturation sensing circuit will reset the integrating circuit to offset any artifact signal and thereby minimize loss of the desired ECG signal as a result of the artifact.

The transfer function of the integrating circuit, relating $e_4$ to $e_3$, is expressed as follows:

$$\frac{e_4}{e_3} = \frac{-1}{1 + \frac{1}{R_5C_1s}} = \frac{-s}{s + \frac{1}{R_5C_1}} \quad \text{Eq. (3)}$$

The time function related to this transfer function is:

$$\frac{e_4}{e_3}(t) = -e^{\frac{-t}{R_5C_1}} \quad \text{Eq. (4)}$$

$R_5C_1$ = about 3.3 seconds

Therefore, at very low frequencies or at DC, the gain is substantially zero, while at frequencies above $$f_c = \frac{1}{2\pi R_5 C_1}$$

Hz.
is substantially unity.

The time constant $R_5 C_1$ is about 3.3 seconds. Therefore, $f_c$ equals 0.0482 Hz. Note that $R_5 = 3.3$ megohms.

The amplifier 132, with its associated resistor values, has a gain of about $$\frac{1000}{6.65} = 150.4$$

Therefore, the gain of the entire ECG amplification circuitry of FIGS. 1a and 1b, in the pass band, $$\frac{e_7}{e_2 - e_1} = 6.63 \times 1 \times 150.4 = 997$$

The diodes 152, 154 comprise the saturation sensing circuit. When $e_7$ is 2.5 volts above or 2.5 volts below the reference level, the diodes 152, 154 will conduct and cause the integration circuit 134 to reset quickly. When the diodes are conducting, the transfer function is as follows:

$$\frac{e_4}{e_3} = \frac{-1}{1 + \frac{150}{22.5 \times 10^3 C_1 s}} = \frac{-s}{s + \frac{150}{22.5 \times 10^3 C_1}} = \frac{-s}{s + 6667} \quad \text{Eq. (5)}$$

The time constant is now 150 microseconds.

Therefore, the fast acting saturation sensing circuit changes the amplifier time constant from about 3 seconds to 61 microseconds. This allows the amplifier 130 to rapidly offset any input DC transient caused by the artifact signals. As a consequence, a negligible amount of ECG signal is lost while transient compensation takes place. The saturation sensing circuit is only active long enough to reset the integrating circuit 134 to a new operating point, to offset the artifact.

While the invention herein has been described with some particularity, it is to be understood that those of ordinary skill in the art may be able to make certain additions or modifications to, or deletions from, the embodiment described herein without departing from the spirit of the scope of the invention, as set forth in the appended claims.

I claim:

1. An ECG system comprising:
   (a) a plurality of electrodes adapted for sensing electrical signals produced by the body of a living subject;
   (b) a separate electrical cable attached to each electrode;
   (c) an acquisition unit coupled to a power source and comprising:
      (i) a differential preamplifier stage adapted for coupling to two of said cables for producing an output signal which is a function of a difference between the electrical signals appearing at the corresponding two of said electrodes;
      (ii) a main amplifier stage downstream from said differential preamplifier stage and being DC coupled to receive the output of said preamplifier stage;
      (iii) a time integrating circuit and control circuitry coupled to a location between said amplifier stages for automatically adjusting the overall gain of said preamplifier and main amplifier stages as a function of frequency to exhibit a low frequency roll off from a positive gain down to approximately zero at DC, said low frequency roll off beginning at less than 1 Hz.

2. The ECG system of claim 1, wherein:
   said low frequency roll off begins at approximately 0.05 Hz.

3. The system of claim 1, further comprising:
   saturation sensing circuitry coupled to said integrating circuitry to reset said integrating circuit to offset an artifact signal.

4. A heart monitoring system comprising:
   (a) two electrodes adapted for attachment to a patient's body;
   (b) a separate electrically conductive cable coupled to each electrode;
   (c) a differential preamplifier stage couplable to a power source and coupled to receive inputs from each of said electrodes via said cables and for producing an output which is a function of the instantaneous difference between electrical signals on the two electrodes;
   (d) a main amplifier stage couplable to the power source and DC coupled to receive the output from said preamplifier stage;
   (e) circuitry for automatically varying the gain of said main amplifier stage with respect to frequency between substantially zero at DC and a positive value over a low frequency range, and
   (f) circuitry for processing an output of said main amplifier stage to produce a tangible representation of electrical signals appearing at said electrodes.

5. The system of claim 4, wherein said circuitry for varying the low frequency gain response of the main amplifier stage comprises integrating circuitry.

6. The system of claim 5, further comprising:
   a saturation sensing circuit responsive to excursions of the output of said main amplifier stage outside a range to reset an operating point of said integrating circuitry.

7. The system of claim 6, wherein said saturation sensing circuit comprises a pair of diodes.

8. The system of claim 5, wherein said integrating circuit and said main amplifier stage together define a gain versus frequency characteristic having a roll-off located at about 0.05 Hz.

9. The system of claim 4, wherein said circuitry for processing an output of said main amplifier stage comprises a voltage controlled oscillator.

10. The system of claim 4, further comprising:
    circuitry for producing a constant test signal and for applying said test signal to a portion of said preamplifier stage for facilitating circuit adjustment in the absence of input signals occurring at said electrodes.

11. The system of claim 4, further comprising:
    a cathode ray tube coupled to the output of said main amplifier stage.

12. The system of claim 4, further comprising:
    a recorder coupled to receive the output of said main amplifier stage for facilitating storage of data represented by electrical signals appearing at said electrodes.

13. The system of claim 4, further comprising a source couplable to said amplifiers and including a battery, an integrated circuit constant current device coupled to the battery, and a precision resistance coupled in series with said constant current device.

14. A heart monitoring system comprising:
(a) two electrodes adapted for attachment to a patient's body;
(b) a separate electrically conductive cable coupled to each electrode;
(c) a differential preamplifier stage couplable to a power source and coupled to receive inputs from each of said electrodes via said cables and for producing an output which is a function of the instantaneous difference between electrical signals on the two electrodes;
(d) a main amplifier stage couplable to a power source and DC coupled to receive an output from said preamplifier stage;
(e) an adjustable gain amplifier coupled between said preamplifier stage and said main amplifier stage;
(f) circuitry for automatically adjusting the gain of said variable gain amplifier as a function of frequency between a positive value of gain above a low frequency roll off value and a gain of substantially zero at DC, and
(g) circuitry for processing an output of said main amplifier stage to provide a tangible representation of electrical signals appearing at said electrodes.

15. The system of claim 14, wherein:
said low frequency roll off frequency value is approximately 0.05 Hz.

16. The system of claim 14, wherein said gain adjusting circuitry comprises an integrating circuit.

17. The system of claim 16, wherein said integrating circuit comprises:
an operational amplifier having capacitor feedback and a resistor input.

18. The system of claim 14, wherein said gain adjusting circuitry comprises:
a DC integrator for controlling the low frequency response of the system.

* * * * *